(12) United States Patent
Gunn et al.

(10) Patent No.: US 11,696,777 B2
(45) Date of Patent: Jul. 11, 2023

(54) COMPACT SYSTEM USED TO DETERMINE TISSUE OR ARTIFACT CHARACTERISTICS

(71) Applicant: Briteseed LLC, Chicago, IL (US)

(72) Inventors: Jonathan Gunn, Chicago, IL (US); Steve McPhilliamy, Chicago, IL (US); Hariharan Subramanian, Mundelein, IL (US); Paul Le Rolland, Chicago, IL (US); Amal Chaturvedi, Chicago, IL (US); Keith A. Grider, Chicago, IL (US); Daniel J. Greene, Chicago, IL (US); Sean Corrigan, Chicago, IL (US); Tomas Matusaitis, Chicago, IL (US); Marcus Stephen Papadopoulos, Paradise Valley, AZ (US)

(73) Assignee: Briteseed, LLC, Chicago, IL (US)

( * ) Notice: Subject to any disclaimer, the term of this patent is extended or adjusted under 35 U.S.C. 154(b) by 0 days.

(21) Appl. No.: 16/955,675

(22) PCT Filed: Dec. 21, 2018

(86) PCT No.: PCT/US2018/067069
§ 371 (c)(1),
(2) Date: Jun. 18, 2020

(87) PCT Pub. No.: WO2019/126633
PCT Pub. Date: Jun. 27, 2019

(65) Prior Publication Data
US 2021/0068856 A1 Mar. 11, 2021

Related U.S. Application Data

(60) Provisional application No. 62/609,746, filed on Dec. 22, 2017.

(51) Int. Cl.
*A61B 17/29* (2006.01)
*A61B 17/00* (2006.01)

(52) U.S. Cl.
CPC .... *A61B 17/29* (2013.01); *A61B 2017/00526* (2013.01); *A61B 2017/2926* (2013.01)

(58) Field of Classification Search
CPC .......... A61B 17/29; A61B 2017/00526; A61B 2017/2926; A61B 5/489; A61B 5/0084; A61B 5/1459; A61B 5/6847
See application file for complete search history.

(56) References Cited

U.S. PATENT DOCUMENTS

| 5,129,400 A | 7/1992 | Makino et al. |
| 5,259,761 A | 11/1993 | Schnettler et al. |

(Continued)

FOREIGN PATENT DOCUMENTS

| EP | 1870034 | 12/2007 |
| EP | 2 353 534 | 8/2011 |

(Continued)

OTHER PUBLICATIONS

International Search Report and Written Opinion, counterpart PCT application PCT/US2018/067069, 17 pages (dated May 27, 2019).

(Continued)

*Primary Examiner* — Brooke Labranche
(74) *Attorney, Agent, or Firm* — Cook Alex Ltd.

(57) ABSTRACT

A surgical system includes a tubular shaft having a wall defining an outer surface and an inner surface disposed about an inner space, the tubular shaft having a proximal end and a distal end. The surgical system also includes at least one light emitter and at least one light sensor disposed at the distal end of the tubular shaft, and one or more leads or conductors electrically coupled to the at least one light emitter or the at least one light sensor. The one or more leads may be disposed in clearances defined by first and second jaws. Alternatively or in addition, the one or more conductors may be formed on a flexible substrate, and the flexible (Continued)

substrate may have a deformed state in which the substrate is disposed in the inner space.

9 Claims, 9 Drawing Sheets

(56) References Cited

U.S. PATENT DOCUMENTS

| | | |
|---|---|---|
| 5,762,609 A | 6/1998 | Benaron et al. |
| 5,769,791 A | 6/1998 | Benaron et al. |
| 5,772,597 A | 6/1998 | Goldberger et al. |
| 5,785,658 A | 7/1998 | Benaron et al. |
| 5,807,261 A | 9/1998 | Benaron et al. |
| 5,987,346 A | 11/1999 | Benaron et al. |
| 6,178,340 B1 | 1/2001 | Svetliza |
| 6,374,128 B1 | 4/2002 | Toida et al. |
| 6,569,104 B2 | 5/2003 | Ono et al. |
| 6,594,518 B1 | 7/2003 | Benaron et al. |
| 6,922,577 B2 | 7/2005 | Nakashima et al. |
| 7,006,861 B2 | 2/2006 | Flock et al. |
| 7,112,201 B2 | 9/2006 | Truckai et al. |
| 7,235,072 B2 | 6/2007 | Sartor et al. |
| 7,515,265 B2 | 4/2009 | Alfano et al. |
| 7,740,591 B1 | 6/2010 | Starr et al. |
| 7,749,217 B2 | 7/2010 | Podhajsky |
| 7,904,138 B2 | 3/2011 | Goldman et al. |
| 7,983,738 B2 | 7/2011 | Goldman et al. |
| 8,058,771 B2 | 11/2011 | Giordano et al. |
| 8,073,531 B2 | 12/2011 | Goldman et al. |
| 8,118,206 B2 | 2/2012 | Zand et al. |
| 8,123,745 B2 | 2/2012 | Beeckler et al. |
| 8,150,500 B2 | 4/2012 | Goldman et al. |
| 8,244,333 B2 | 8/2012 | Wood et al. |
| 8,255,040 B2 | 8/2012 | Goldman et al. |
| 8,295,904 B2 | 10/2012 | Goldman et al. |
| 8,380,291 B2 | 2/2013 | Wood et al. |
| 8,391,960 B2 | 3/2013 | Wood et al. |
| 8,417,306 B2 | 4/2013 | Cheng |
| 8,463,364 B2 | 6/2013 | Wood et al. |
| 8,467,857 B2 | 6/2013 | Kim et al. |
| 8,478,386 B2 | 7/2013 | Goldman et al. |
| 8,483,805 B2 | 7/2013 | Takenoshita et al. |
| 8,483,819 B2 | 7/2013 | Choi et al. |
| 8,489,178 B2 | 7/2013 | Wood et al. |
| 8,586,924 B2 | 11/2013 | Demos |
| 8,649,568 B2 | 2/2014 | Sato |
| 8,649,848 B2 | 2/2014 | Crane et al. |
| 8,682,418 B2 | 3/2014 | Tanaka |
| 8,706,200 B2 | 4/2014 | Goldman et al. |
| 8,712,498 B2 | 4/2014 | Goldman et al. |
| 8,750,970 B2 | 6/2014 | Goldman et al. |
| 8,792,967 B2 | 7/2014 | Sato |
| 8,818,493 B2 | 8/2014 | Goldman et al. |
| 8,838,210 B2 | 9/2014 | Wood et al. |
| 9,526,921 B2 | 12/2016 | Kimball et al. |
| 2002/0169381 A1 | 11/2002 | Asada et al. |
| 2003/0036685 A1 | 2/2003 | Goodman |
| 2003/0036751 A1 | 2/2003 | Anderson et al. |
| 2003/0120306 A1 | 6/2003 | Burbank et al. |
| 2004/0044363 A1* | 3/2004 | Fowler ............... A61B 17/1285 606/205 |
| 2004/0111085 A1 | 6/2004 | Singh |
| 2005/0021027 A1 | 1/2005 | Shields et al. |
| 2005/0143662 A1 | 6/2005 | Marchitto et al. |
| 2005/0180620 A1 | 8/2005 | Takiguchi |
| 2006/0020212 A1 | 1/2006 | Xu et al. |
| 2006/0052850 A1 | 3/2006 | Darmos et al. |
| 2006/0100523 A1 | 5/2006 | Ogle et al. |
| 2006/0155194 A1 | 7/2006 | Marcotte et al. |
| 2007/0038118 A1 | 2/2007 | DePue et al. |
| 2007/0299468 A1* | 12/2007 | Viola .................. A61B 5/0084 606/205 |
| 2009/0018414 A1 | 1/2009 | Toofan |
| 2009/0054908 A1 | 2/2009 | Zand et al. |
| 2010/0222786 A1 | 9/2010 | Kassab |
| 2010/0249763 A1 | 9/2010 | Larson et al. |
| 2011/0021925 A1 | 1/2011 | Wood et al. |
| 2011/0245685 A1 | 10/2011 | Murata et al. |
| 2012/0016362 A1 | 1/2012 | Heinrich et al. |
| 2012/0046555 A1 | 2/2012 | Takamatsu et al. |
| 2012/0143182 A1 | 6/2012 | Ullrich et al. |
| 2012/0172842 A1 | 7/2012 | Sela et al. |
| 2012/0296205 A1 | 11/2012 | Chernov et al. |
| 2013/0102905 A1 | 4/2013 | Goldman et al. |
| 2013/0226013 A1 | 8/2013 | McEwen et al. |
| 2013/0267874 A1 | 10/2013 | Marcotte et al. |
| 2014/0086459 A1 | 3/2014 | Pan et al. |
| 2014/0100455 A1 | 4/2014 | Goldman et al. |
| 2014/0155753 A1 | 6/2014 | McGuire, Jr. et al. |
| 2014/0194751 A1 | 7/2014 | Goldman et al. |
| 2014/0236019 A1 | 8/2014 | Rahum |
| 2014/0276088 A1 | 9/2014 | Drucker |
| 2014/0277106 A1 | 9/2014 | Crews et al. |
| 2014/0313482 A1 | 10/2014 | Shahidi et al. |
| 2015/0011896 A1 | 1/2015 | Yelin et al. |
| 2015/0051460 A1 | 2/2015 | Saxena et al. |
| 2015/0066000 A1 | 3/2015 | An et al. |
| 2017/0079740 A1 | 3/2017 | Hufnagel et al. |
| 2017/0172550 A1* | 6/2017 | Mukherjee ............ A61B 17/00 |
| 2017/0181071 A1 | 6/2017 | Fehrenbacher et al. |
| 2017/0367772 A1 | 12/2017 | Gunn et al. |
| 2018/0042522 A1 | 2/2018 | Subramanian et al. |
| 2018/0098705 A1 | 4/2018 | Chaturvedi et al. |
| 2018/0289315 A1 | 10/2018 | Chaturvedi et al. |
| 2019/0038136 A1 | 2/2019 | Gunn et al. |
| 2019/0046220 A1 | 2/2019 | Chaturvedi et al. |
| 2019/0175158 A1 | 6/2019 | Chaturvedi et al. |
| 2020/0268311 A1 | 8/2020 | Shukair et al. |
| 2020/0337633 A1 | 10/2020 | Chaturvedi et al. |
| 2020/0345297 A1 | 11/2020 | Chaturvedi et al. |

FOREIGN PATENT DOCUMENTS

| | | |
|---|---|---|
| EP | 3181040 | 6/2017 |
| GB | 1 445 678 | 8/1976 |
| JP | H07-255735 | 10/1995 |
| JP | H10-005245 | 1/1998 |
| JP | 2003-019116 | 1/2003 |
| JP | 2005-058553 | 3/2005 |
| JP | 2010-081972 | 4/2010 |
| JP | 2010-264260 | 11/2010 |
| JP | 2016-518171 | 6/2016 |
| WO | WO98/27865 | 7/1998 |
| WO | WO2001/060427 | 8/2001 |
| WO | WO2003/039326 | 5/2003 |
| WO | WO2004/030527 | 4/2004 |
| WO | WO2005/091978 | 10/2005 |
| WO | WO2008/082992 | 7/2008 |
| WO | WO2009/144653 | 12/2009 |
| WO | WO2011/013132 | 2/2011 |
| WO | WO2012/158774 | 11/2012 |
| WO | WO2013/134411 | 9/2013 |
| WO | WO2014/194317 | 12/2014 |
| WO | WO2015/148504 | 10/2015 |
| WO | WO2016/134327 | 8/2016 |
| WO | WO2016/134330 | 8/2016 |
| WO | WO2017/062720 | 4/2017 |
| WO | WO2017/139624 | 8/2017 |
| WO | WO2017/139642 | 8/2017 |
| WO | WO2018/044722 | 3/2018 |
| WO | WO2019/050928 | 3/2019 |
| WO | WO2019/143965 | 7/2019 |
| WO | WO2020/041203 | 2/2020 |
| WO | WO2020/142394 | 7/2020 |

OTHER PUBLICATIONS

Akl et al., Performance Assessment of an Opto-Fluidic Phantom Mimicking Porcine Liver Parenchyma, J. Bio. Optics, vol. 17(7) 077008-1 to 077008-9 (Jul. 2012).

Comtois et al., A Comparative Evaluation of Adaptive Noise Cancellation Algorithms for Minimizing Motion Artifacts in a

(56) References Cited

OTHER PUBLICATIONS

Forehead-Mounted Wearable Pulse Oximeter, Conf. Proc. IEEE Eng. Med. Biol. Soc., 1528-31 (2007).

Figueiras et al., Self-Mixing Microprobe for Monitoring Microvascular Perfusion in Rat Brain, Med. Bio. Eng'r Computing 51:103-112 (Oct. 12, 2012).

Hammer et al., A Simple Algorithm for In Vivo Ocular Fundus Oximetry Compensating for Non-Haemoglobin Absorption and Scattering, Phys. Med. Bio. vol. 47, N233-N238 (Aug. 21, 2002).

Ibey et al., Processing of Pulse Oximeter Signals Using Adaptive Filtering and Autocorrelation to Isolate Perfusion and Oxygenation Components, Proc SPIE, vol. 5702, 54-60 (2005).

Li et al., Pulsation-Resolved Deep Tissue Dynamics Measured with Diffusing-Wave Spectroscopy, Optics Express, vol. 14, No. 17, 7841-7851 (Aug. 21, 2006).

Mendelson et al., In-vitro Evaluation of a Dual Oxygen Saturation/Hematocrit Intravascular Fiberoptic Catheter, Biomed Instrum. Technol. 24(3):199-206 (May/Jun. 1990).

Phelps et al., Rapid Ratiometric Determination of Hemoglobin Concentration using UV-VIS Diffuse Reflectance at Isobestic Wavelengths, Optics Express, vol. 18, No. 18, 18779-18792 (Aug. 30, 2010).

Subramanian, Real Time Perfusion and Oxygenation Monitoring in an Implantable Optical Sensor, Thesis Texas A&M Univ. (Dec. 2004).

Subramanian, Real-Time Separation of Perfusion and Oxygenation Signals for an Implantable Sensor Using Adaptive Filtering, IEEE Trans. Bio. Eng'g, vol. 52, No. 12, 2016-2023 (Dec. 2005).

Subramanian, An Autocorrelation-Based Time Domain Analysis Technique for Monitoring Perfusion and Oxygenation in Transplanted Organs, IEEE Trans. Bio. Eng'g, vol. 52, No. 7, 1355-1358 (Jul. 2005).

Search Report and English-language machine translation, counterpart Japanese App. No. 2020-534481 (dated Dec. 16, 2022) (31 pages).

Notice of Reasons for Refusal and English-language machine translation, counterpart Japanese App. No. 2020-534481 (dated Dec. 20, 2022) (6 pages).

\* cited by examiner

COMPACT SYSTEM USED TO DETERMINE TISSUE OR ARTIFACT CHARACTERISTICS

BACKGROUND

This patent is directed to a system used to determine characteristics of tissue or an artifact, such as a vessel, and in particular to a system used to determine characteristics of tissue or an artifact where the system utilizes a flexible substrate to carry certain components.

Systems and methods that identify artifacts, and in particular vessels, in the surgical field during a surgical procedure provide valuable information to the surgeon or surgical team. U.S. hospitals lose billions of dollars annually in unreimbursable costs because of inadvertent vascular damage during surgery. In addition, the involved patients face a mortality rate of up to 32%, and likely will require corrective procedures and remain in the hospital for an additional nine days, resulting in tens, if not hundreds, of thousands of dollars in added costs of care. Consequently, there is this significant value to be obtained from methods and systems that permit accurate determination of the presence of vessels, such as blood vessels, in the surgical field, such that these costs may be reduced or avoided.

Systems and methods that provide information regarding the presence of blood vessels in the surgical field are particularly important during minimally invasive surgical procedures. Traditionally, surgeons have relied upon tactile sensation during surgical procedures both to identify blood vessels and to avoid inadvertent damage to these vessels. Because of the shift towards minimally invasive procedures, including laparoscopic and robotic surgeries, surgeons have lost the ability to use direct visualization and the sense of touch to make determinations as to the presence of blood vessels in the surgical field. Consequently, surgeons must make the determination whether blood vessels are present in the surgical field based primarily on convention and experience. Unfortunately, anatomical irregularities frequently occur because of congenital anomalies, scarring from prior surgeries, and body habitus (e.g., obesity). Systems and methods that would permit surgeons to determine the presence and/or the characteristics of vessels in the surgical field during surgery (potentially in real time or near real time) under such conditions would be a significant advantage.

On the other hand, while it would be advantageous to include systems and methods that provide information regarding the presence of blood vessels in the surgical field, the adoption of such systems and methods would be impeded if these systems and methods were to complicate the manufacture and/or use of the associated surgical instruments. This is particularly true in the field of minimally-invasive surgery, where surgical instrument design involves a complex balance of competing interests, and space for the integration of new technologies is at a considerable premium.

As set forth in more detail below, the present disclosure describes a user interface embodying advantageous alternatives to the existing systems and methods, which may provide for improved identification for avoidance or isolation of artifacts, such as vessels, without undue complication of the surgical instrument or surgical procedure.

SUMMARY

According to an aspect of the present disclosure, a surgical system includes a tubular shaft having a proximal end and a distal end, a first jaw and a second jaw pivotally attached at the distal end of the tubular shaft, and at least one light emitter and at least one light sensor. The at least one light emitter is attached to the first jaw and the at least one light sensor is attached to the second jaw, each of the at least one light emitter and at least one light sensor coupled to at least one lead. The first and second jaws have inwardly facing surfaces that define at least in part one or more clearances in which the at least one lead coupled to the at least one light emitter and the at least one lead coupled to the at least one light sensor are disposed.

According to another aspect of the present disclosure, a surgical system includes a tubular shaft having a wall defining an outer surface and an inner surface disposed about an inner space, the tubular shaft having a proximal end and a distal end. The surgical system also includes at least one light emitter and at least one light sensor disposed at the distal end of the tubular shaft, and one or more conductors electrically coupled to the at least one light emitter or the at least one light sensor. The one or more conductors are formed on a flexible substrate, and the flexible substrate has a deformed state in which the substrate is disposed in the inner space.

According to yet another aspect of the present disclosure, a method of manufacturing a surgical system includes forming a plurality of conductors on a flexible substrate, and coupling the plurality of conductors to at least one light emitter and at least one light sensor. The method also includes deforming the flexible substrate and disposing the deformed flexible substrate into an inner space of a tubular shaft, the tubular shaft having a proximal end and a distal end and the deformed flexible substrate disposed within the inner space such that the at least one light emitter and the at least one light sensor are disposed at the distal end of the tubular shaft.

According to a further aspect of the present disclosure, a surgical system includes a shaft having a proximal end and a distal end, and a pair of jaws disposed at the distal end of the tubular shaft. The system further includes a flexible substrate on which one or more conductors are disposed, the flexible substrate having a deformed state in which the substrate is attached to the pair of jaws, and at least one light emitter and at least one light sensor electrically coupled to the one or more conductors, such that the at least one light emitter is attached to a first jaw of the pair of jaws and the at least one light sensor is attached to a second jaw of the pair of jaws.

According to a still further aspect of the present disclosure, a method of manufacturing a surgical system, the method including forming one or more conductors on a flexible substrate, coupling the one or more conductors to at least one light emitter and at least one light sensor, and deforming the flexible substrate. The method further includes attaching the deformed flexible substrate to a pair of jaws, such that the light emitter is attached to a first jaw of the pair of jaws and the light sensor is attached to a second jaw of the pair of jaws.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION OF VARIOUS EMBODIMENTS

Figure 1:
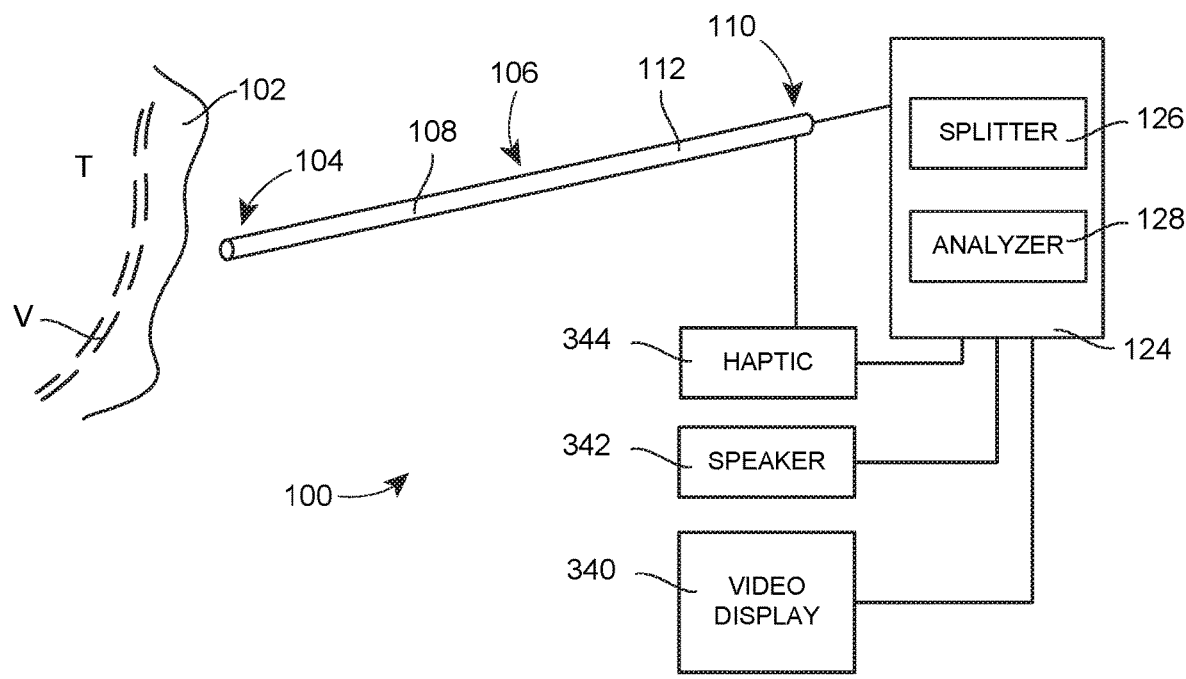
FIG. 1 is a schematic diagram of a surgical system according to an embodiment of the present disclosure.

The embodiments described herein provide structures for use with or in systems used to determine characteristics of tissue and/or artifacts in a surgical field using a light emitter and a light sensor. In particular, the surgical system may include a shaft having a distal end and a proximal end, the proximal end including a grip or handle. The system also includes at least one light emitter and one light sensor attached to the distal end of the shaft. According to certain embodiments, the light emitter and the light sensor each may be attached one of a pair of jaws. A controller may be coupled to at least the at least one light sensor. The surgeon may use the afore-mentioned surgical instrument as part of the procedure, or the surgeon may use the surgical instrument to inspect or survey the surgical field.

In either event, such an instrument with an elongated shaft may be of the type that is used in minimally invasive and robotic surgeries. As such, there is a desire to minimize the dimensions of the opening through which the shaft will be disposed. Minimization of the opening leads to minimization of the external dimensions of the shaft. In turn, the external dimensions of the shaft have an effect on the space available inside the shaft.

As mentioned above, if the incorporation of new technology complicates the surgical instrument or its use, the complexity may well impede adoption of the new technology. Consequently, a system that permits the new technology to have as minimal an impact on the structure, operation and/or use of the instrument is desirable. In particular, with technology that is intended for use in minimally invasive and/or robotic surgeries, it is desirable to minimize the spatial requirements of the new technology and/or to simplify its integration into the overall instrument.

Therefore, a structure that simplifies the coupling of the light emitter/light sensor and the controller without requiring redesign or repackaging of the operating mechanisms, such as the actuation mechanism, of the surgical instrument would be preferable. Moreover, it is desirable if such a solution does not require the inclusion of additional lumens in the elongated member or shaft, because the inclusion of such additional lumens would disturb the arrangement of the existing structures within the shaft. Furthermore, the creation of an elongated member, such as a tubular shaft or a rod, with lumens that extend from the distal end to a proximal end with sufficient precision to permit a wire or other conductor to be disposed along the lumen may present a difficult, if not impossible, manufacturing problem.

In addition, where the surgical instrument includes a pair of jaws, with the light emitter disposed on one of the jaws and the light sensor disposed on the other of the jaws, it would be desirable to provide a system that minimized the effect on the arrangement and operation of the jaws. In particular, it would be desirable if the system limited the complexity of the connections required for the light emitter and/or light sensor relative to the structure and operation of the jaws. Further, it would be desirable if the system limited the overall number of components required, thereby simplifying the method of assembly for the instrument.

A number of embodiments for electrically coupling the light emitter and/or the light sensor and the remainder of the electrical components (e.g., the controller) are proposed that may enhance the adoptability of such technology by maintaining the simplicity of the structure, operation and/or use of the instrument.

In particular, embodiments are illustrated in FIGS. 7-15 wherein a flexible substrate is utilized to simplify the connections between the light emitter/light sensor and the controller. In addition, certain of the embodiments illustrated in FIGS. 7-15 utilize a flexible substrate to simplify the integration of the technology into a two jawed surgical instrument, and in particular a two jawed surgical instrument where at least one of the jaws is moveable relative to a shaft to which the pair of jaws is connected or attached.

This technology may be used with a configuration where the light emitter and light sensor are disposed opposite each other in a transmittance-based configuration, or the light emitter and light sensor may be disposed generally in the same direction in a reflectance-based configuration. Therefore, before discussing the structure, operation and assembly of the embodiments incorporating the flexible substrate, the general structure and operation of the system it described with respect to FIGS. 1-6. These embodiments described below are for purposes of explanation, and not by way of limitation.

A surgical system 100 is illustrated, which system 100 may be used to determine, for example, a characteristic (e.g., presence, diameter, etc.) of a vessel, V, within a region 102 of tissue, T, proximate to a working end 104 of a surgical instrument 106. It will be understood that the vessel V may be connected to other vessels with the region 102 of tissue T, and in addition, the vessel V may extend beyond the region 102 so as to be in fluid communication with other organs (e.g., the heart) also found in the body of the patient. Furthermore, while the tissue T appears in FIGS. 1-6 to surround fully the vessel V (in terms of both circumference and length) to a particular depth, this need not be the case in all instances where the system 100 is used. For example, the tissue T may only partially surround the circumference of and/or only surround a section of the length of the vessel V, or the tissue T may overlie the vessel V in a very thin layer. As further non-limiting examples, the vessel V may be a blood vessel, and the tissue T may be connective tissue, adipose tissue and/or liver tissue.

According to the illustrated embodiments, the working end 104 of the surgical instrument 106 is also a distal end of a shaft 108. Consequently, the working end and the distal end will be referred to as working end 104 or distal end 104. The shaft 108 also has a proximal end 110, and a grip or handle 112 (referred to herein interchangeably as grip 112) is disposed at the proximal end 110 of the shaft 108. The grip 112 is designed in accordance with the nature of the instrument 106; as to the dissector illustrated in FIG. 1, the grip 112 may be defined along a length of the shaft 108, while as to the thermal ligation device illustrated in FIG. 2, the grip 112 may be a pistol-type grip including a trigger 114. As a further alternative, finger rings arranged in a generally scissors-type grip may be used.

While the working or distal end 104 and the proximal end 110 with grip 112 are illustrated as disposed at opposite-most ends of the shaft 108, it will be recognized that certain surgical instruments have working ends (where a tool tip is attached, for example) disposed on the opposite-most ends of the shaft and a gripping region disposed intermediate to the opposite working ends. In accordance with the terms "distal" and "proximal" as used herein, the working ends of such an instrument are referred to herein as the distal ends and the gripping region as the proximal end. Relative to the illustrated embodiments, however, the distal and proximal ends are located at opposite-most (or simply opposite) ends of the shaft 108.

As mentioned above, according to the preferred embodiments illustrated, the surgical system 100 includes a sensor with at least one light emitter 120 (or simply the light emitter 120) and at least one light sensor or detector 122 (or simply the light sensor 122). See FIGS. 3-6. According to the illustrated embodiments, a controller 124 is coupled to the light emitter 120 and the light sensor 122, which controller 124 may include a splitter 126 and an analyzer 128 as explained below. See FIGS. 1 and 2.

Figure 3:
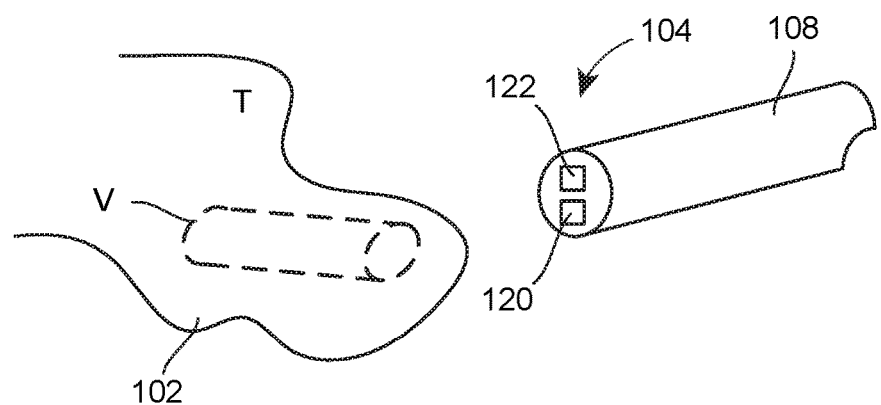
FIG. 3 is an enlarged, fragmentary view of a reflectance-based embodiment of the surgical instrument of FIG. 1 with light emitter and light sensor with fixed spacing, and a section of a vessel illustrated as proximate the light emitter and light sensor.
Figure 4:
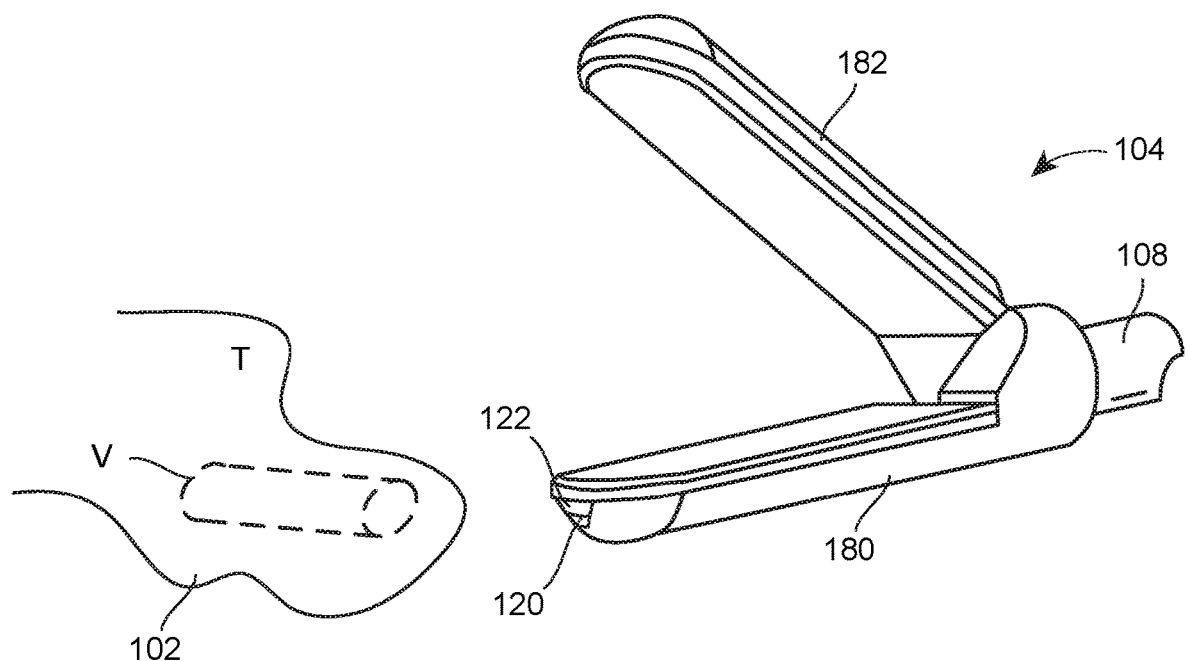
FIG. 4 is an enlarged, fragmentary view of a reflectance-based embodiment of the surgical instrument of FIG. 2 with light emitter and light sensor with fixed spacing, and a section of an vessel illustrated as proximate the light emitter and light sensors.
Figure 5:
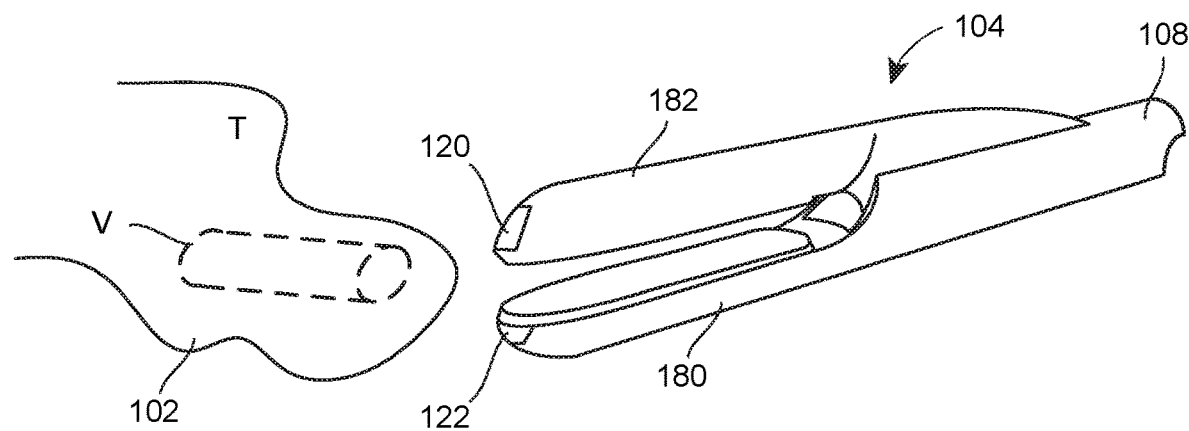
FIG. 5 is an enlarged, fragmentary view of another reflectance-based embodiment of the surgical instrument of FIG. 2 with light emitter and light sensor having an adjustable spacing relative to each other, and a section of a vessel illustrated as proximate the light emitter and light sensor.
Figure 6:
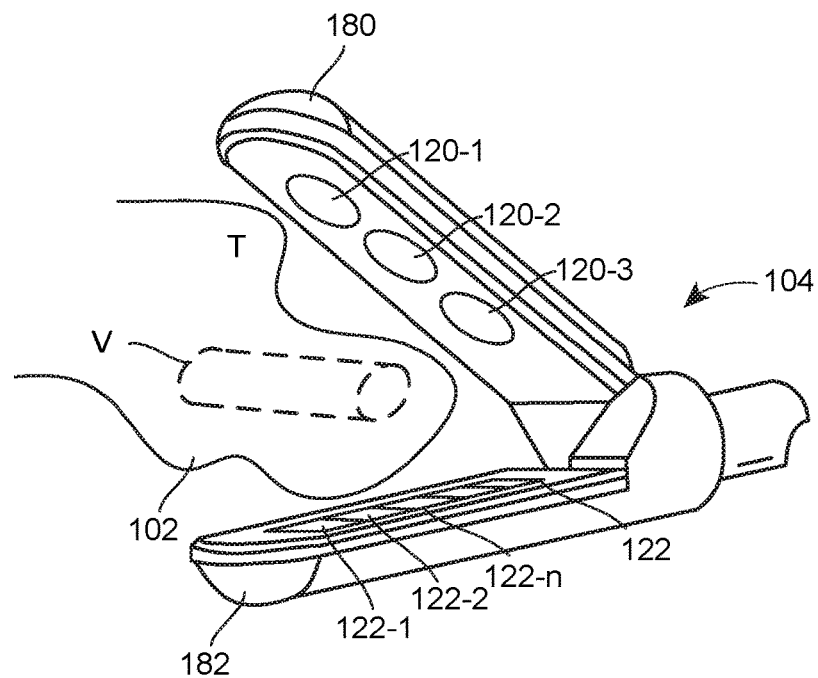
FIG. 6 is an enlarged, fragmentary view of a transmittance-based embodiment of the surgical instrument of FIG. 2 with light emitters and light sensors, and a section of a vessel illustrated as disposed between the light emitters and light sensors.

The light emitter 120 is disposed at the working end 104 of the surgical instrument 106. The light sensor 122 is also disposed at the working end 104 of the surgical instrument 106. As illustrated in FIGS. 3 and 4, the system 100 may operate according to a reflectance-based approach, such that the light emitter 120 and the light sensor 122 may face in a common direction and with fixed spacing therebetween, for example on a blunt end of a laparoscopic dissection tool or dissector (FIG. 3) or on a single jaw of a two-jaw device, such as a thermal ligation device (FIG. 4), although the relative angle between the light emitter 120 and light sensor 122 may be fixed or variable. The light emitter 120 and the light sensor 122 of a reflectance-based system may be constructed such that the spacing between the light emitter 120 and the light sensor 122 may be adjusted, for example by positioning the light emitter 120 at the end or tip of one of the jaws of a two-jaw device and the light sensor 122 at the end or tip of the other the jaws of the two jaw device, as illustrated in FIG. 5. Alternatively, the system 100 may operate according to a transmittance-based approach, such that the light sensor(s) 122 is/are disposed opposite and facing the light emitter(s) 120, for example on opposite jaws of a surgical instrument 106 as illustrated in FIG. 6.

The light emitter 120 may be adapted to emit light of at least one wavelength. For example, the light emitter 120 may emit light having a wavelength of 660 nm. This may be achieved with a single element, or a plurality of elements (which elements may be arranged or configured into an array, for example, as explained in detail below). In a similar fashion, the light sensor 122 is adapted to detect light at the at least one wavelength (e.g., 660 nm). According to the embodiments described herein, the light sensor 122 includes a plurality of elements, which elements are arranged or configured into an array.

According to certain embodiments, the light emitter 120 may be configured to emit light of at least two different wavelengths, and the light sensor 122 may be configured to detect light at the at least two different wavelengths. As one example, the light emitter 120 may emit and the light sensor 122 may detect light in the visible range and light in the near-infrared or infrared range. Specifically, the light emitter 120 may emit and the light sensor 122 may detect light at 660 nm and at 910 nm. Such an embodiment may be used, for example, to ensure optimal penetration of blood vessel V and the surrounding tissue T under in vivo conditions.

Depending upon the effect of changes in blood flow, light of a third wavelength may also be emitted and sensed. That is, if the method of detection is found to be sensitive to varying rates of blood flow in the vessel of interest, light at 810 nm (i.e., at the isobestic point) may be emitted and sensed to permit normalization of the results to limit or eliminate the effects of changes in blood flow rate.

According to some embodiments, the individual light sensor 122 is adapted to generate a signal comprising a first pulsatile component and a second non-pulsatile component. It will be recognized that the first pulsatile component may be an alternating current (AC) component of the signal, while the second non-pulsatile component may be a direct current (DC) component. Where the light sensor 122 is in the form of an array, the pulsatile and non-pulsatile information may be generated for each element of the array, or at least for each element of the array that defines the at least one row of the array.

As to the pulsatile component, it will be recognized that a blood vessel may be described as having a characteristic pulsation of approximately 60 pulses (or beats) per minute. While this may vary with the patient's age and condition, the range of pulsation is typically between 60 and 100 pulses (or beats) per minute. The light sensor 122 will produce a signal (that is passed to the controller 124) with a particular AC waveform that corresponds to the movement of the blood through the vessel. In particular, the AC waveform corresponds to the light absorbed or reflected by the pulsatile blood flow within the vessel. On the other hand, the DC component corresponds principally to light absorbed, reflected and/or scattered by the superficial tissues.

According to such embodiments, the controller 124 is coupled to the light sensor 122, and may include a splitter 126 to separate the first pulsatile component from the second non-pulsatile component for each element of the light sensor array 122. The controller 124 may also include an analyzer 128 to determine the presence of and/or characteristic(s) of the vessel V within the region 102 proximate to the working end 104 of the surgical instrument 106 based (at least in part) on the pulsatile component.

As mentioned above, the embodiments described herein may include a structure to connect the emitter 120/sensor 122 with the controller 124. FIGS. 7-10 illustrate embodiments that provide such a structure that may simplify the manufacture of the connections, as well as the assembly of the instrument 106. Further, the embodiment may reduce or simplify the spatial requirements of the conductors that form the connections.

Figure 7:
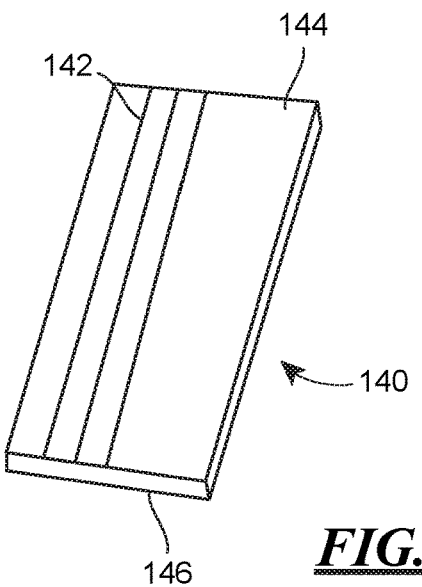
FIG. 7 is an enlarged, perspective view of a flexible substrate with a plurality of conductors formed thereon.
Figure 8:
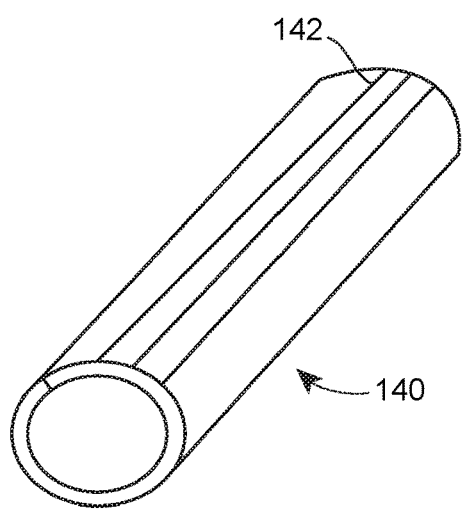
FIG. 8 is an enlarged, perspective view of the substrate of FIG. 7 folded into a curved shape in a deformed state.
Figure 10:
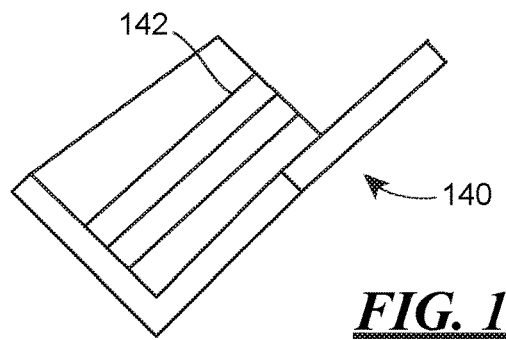
FIG. 10 is an enlarged, perspective view of the substrate of FIG. 7 folded into a bent or angled shape in a deformed state.

According to this embodiment, a flexible substrate 140 is provided. The substrate 140 may have an initially planar state, as illustrated in FIG. 7. The flexible substrate 140 has a deformed state, as illustrated in FIG. 8 or 10. In this deformed state, the substrate 140 may have a curved shape in cross-section, such as illustrated in FIG. 8. The curved shape may be open, in the form of an arc for example, or closed, in the form of a circle or ellipse. Alternative, the substrate 140 may have a deformed state that is bent, angled or angular in cross-section, such as illustrated in FIG. 10. Other shapes are also possible.

Figure 9:
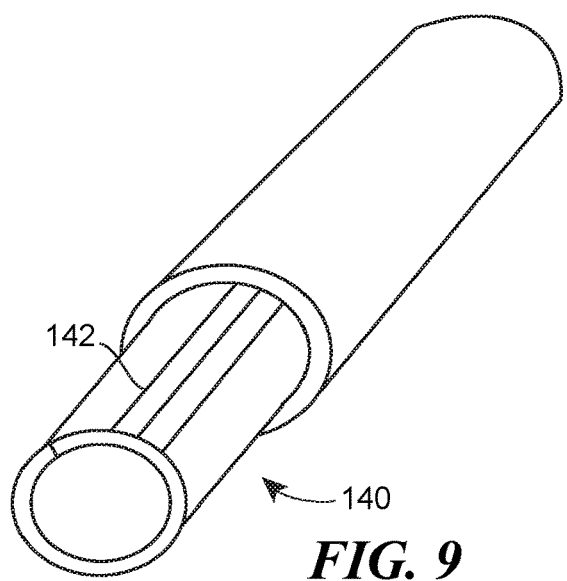
FIG. 9 is an enlarged, perspective view of the folded substrate of FIG. 7 being disposed in an inner space of a hollow shaft.

The shape of the substrate 140 in the deformed state may be a shape that the substrate 140 assumes after the substrate 140 is subjected to a deforming process, such as folding or rolling. The substrate 140 may maintain the deformed state once the deforming process has been applied, or the deforming process may be used to form the substrate 140 into a particular shape prior to insertion into a support or supporting structure. For example, an example of a support or supporting structure is illustrated in FIG. 9, in the form of a hollow or tubular shaft. Such a support could assist in maintaining the substrate in a curved shape.

The substrate 140 need not be formed into a shape that conforms to the general shape of the support, however. The substrate may be formed into a shape that is convenient for insertion, and then may assume a shape in the deformed state as a consequence of the structure of the support. For example, the substrate 140 may be rolled in a spiral cross-section of smaller external dimension of an internal diameter of a hollow or tubular shaft for insertion, and the substrate 140 may be permitted to expand from this intermediate state into its deformed state wherein it abuts the inner surface of the shaft (e.g., as illustrated in FIG. 9). In such an embodiment, the substrate 140 may closely approximate or conform to the inner surface of the support. If the inner surface of the support (e.g., hollow shaft) is circular in cross-section, then the cross-section of the substrate may be curved (or even circular) as well.

According to the embodiments illustrated in FIGS. 7-10, the substrate may have a planar state and a deformed state. This is advantageous from the standpoint of manufacturing structures on the substrate. The structures, such as one or more conductors 142, may be formed on the planar substrate using traditional processes wherein conductive traces, pads, etc. are etched from a layer of material applied to a first surface 144 of the substrate (which may be referred to as the upper side for convenience sake considering the orientation of the substrate 140 in FIG. 7, but not by way of limitation). It is possible to form structures on both sides of the substrate, and thus one or more conductors could be formed on the second, or opposite, surface 146 (which may be referred to as the lower side for convenience sake considering the orientation of the substrate 140 in FIG. 7, but not by way of limitation) instead or as well. Other methods of forming the conductive traces, pads, etc. may also be used, for example additive processes where the conductive traces, pads, etc. are formed by applying a layer of conductive material as is necessary, instead of removing unwanted or unnecessary material. Once the conductors have been defined on one or both surfaces 144, 146, the substrate 140 may be deformed (e.g., rolled or bent).

According to one embodiment, the substrate may be comprised of DuPont Pyralux AP. This material is made of a copper-covered steel and polyimide composite (polyimide and copper foil). The material offers acceptable resistance to high temperatures (with an operating temperature up to 180° C.). Thickness of a substrate made of DuPont Pyralux AP may range for certain embodiments from approximately 34.4 µm to approximately 222.4 µm, depending on the thickness of the dielectric (1 mil to 6 mil—25.4 um to 152.4 um) and the copper traces (0.25 oz./ft2 to 2 oz./ft2—9 um to 70 um). FR4 stiffener may be added to the substrate under the components to prevent the flex from bending, and potentially breaking, the components' connections (e.g., solder joints).

In addition to having on or more conductors 142 formed on the flexible substrate 140, the emitter 120 or sensor 122 may be mounted on the flexible substrate. In particular, the substrate 140 may have one or more pads formed thereon, and the emitter 120 and/or sensor 122 may be attached to those pads such that the emitter 120 and/or sensor 122 are supported on the substrate 140. According to alternative embodiments, the emitter 102 and/or sensor 122 may be attached to the conductors formed on the substrate 140, but not supported on the substrate 140 (e.g., the emitter 102 and/or sensor 122 may be cantilevered from the substrate 140). Either option is possible, as are other alternatives.

Several embodiments are illustrated in FIGS. 11-15 wherein the emitter 120 and/or sensor 122 are attached to the substrate. This arrangement of emitter 120, sensor 122 and substrate may simplify the fabrication of the system, in that the formation of the conductive traces on the substrate may permit the elimination of a significant number of wires that would otherwise be required to connect the emitter 120 and/or sensor 122 to the controller 124. Additionally, the attachment of the emitter 120 and/or sensor 122 to the flexible substrate may permit the fabrication of a subassembly that can move with one or both of a pair of jaws, thereby simplifying the assembly of the system as well.

Figure 11:
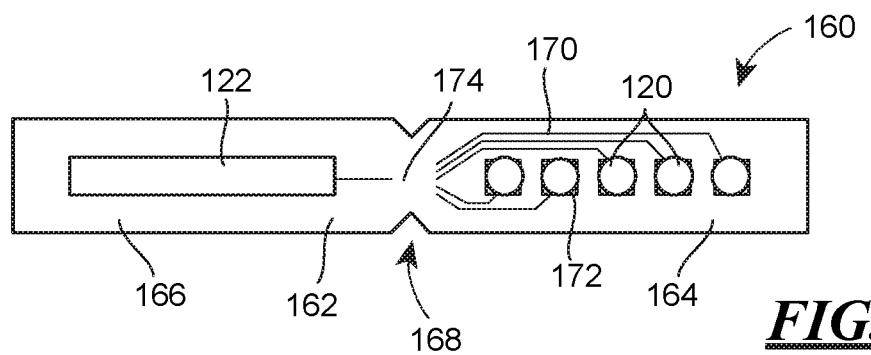
FIG. 11 is an enlarged, plan view of a flexible substrate with at least one light emitter and at least one light sensor formed thereon.
Figure 12:
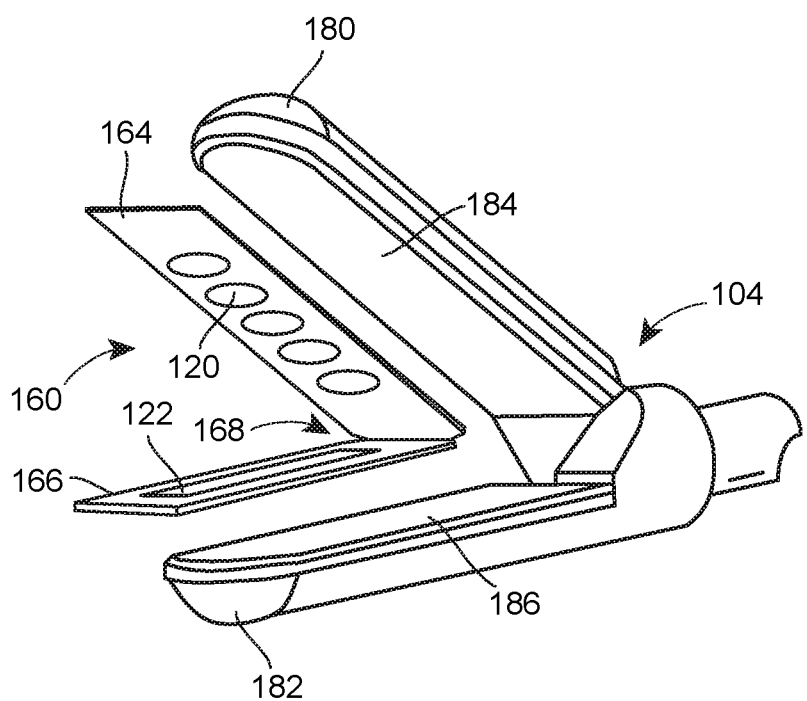
FIG. 12 is an enlarged, side view illustrating how the flexible substrate of FIG. 11 may be assembled with a two-jaw surgical instrument.

A first embodiment is illustrated in FIGS. 11 and 12. According to this embodiment, a subassembly 160 includes a flexible substrate 162 having a first section 164 and a second section 166. The first section 164 and the second section 166 are joined at a living hinge 168, which is also defined by the substrate 162. The substrate 162 may have one or more conductors 170 formed thereon, with one or more conductive pads 172 coupled to the one or more conductors. One or more wires may be attached to the conductors 170, while the emitters 120 are attached to a first set of pads 172 and the sensor 122 (in the form of a sensor array, such as a linear sensor array) is attached to a second set of pads.

In the illustrated embodiment, the first and second sections 164, 166 are approximately equal in length, because the jaws 180, 182 to which the sections 164, 166 are attached are also approximately equal in length. According to other embodiments, the first and second sections 164, 166 may be of unequal length. The first and second sections 164, 166 are also of equal width, again because of the dimensions of the jaws 180, 182 to which the sections 164, 166 are attached. Again, according to other embodiments, the first and second sections 164, 166 may be of unequal width. As illustrated, the first and second sections 164, 166 are approximately rectangular in shape, with the one or the shorter ends of each of the first and second sections 164, 166 attached at the living hinge 168. Here as well, other shapes for the sections 164, 166 may be possible.

The living hinge 168 is formed by a bridge 174 of substrate 160 that connects the first and second sections 162, 164. The width of the bridge 174 may be smaller than the width of the first and second sections to permit greater flexibility in the region of the living hinge 168. To this end, portions of the ends (e.g., notches) of the first and second sections 162, 164 may be removed. Alternatively, the bridge 174 may be formed with a smaller (or narrower) width than the first and second sections 162, 164. The living hinge 168 permits the subassembly including the emitter 120 and sensors 122 to move with the jaws 180, 182.

According to this embodiment, the conductors 170 and pads 172 may be formed on the substrate 160 with the substrate 160 in its planar state in FIG. 11. The emitter 120 and sensors 122 also may be attached to the pads 172 with the substrate 160 in its planar state. The substrate 160 may then be deformed about the living hinge 168 for assembly with the remainder of the instrument 106. The deformed substrate 160 is then attached to the jaws 180, 182 of the instrument 106 (e.g., surfaces 184, 186), whereupon the flexible nature of the substrate 160, and in particular the bridge 174, permits the subassembly to move in accordance with the motion of the jaws 180, 182.

While the embodiment of FIGS. 11 and 12 utilizes the flexible substrate to mount the emitter 120 and sensor 122 while connecting the subassembly to the controller 124 via one or more wires, it is possible to use the flexible substrate to connect the subassembly to the controller 124 as well. The embodiments of FIGS. 13-15 illustrate such an embodiment.

Figure 13:
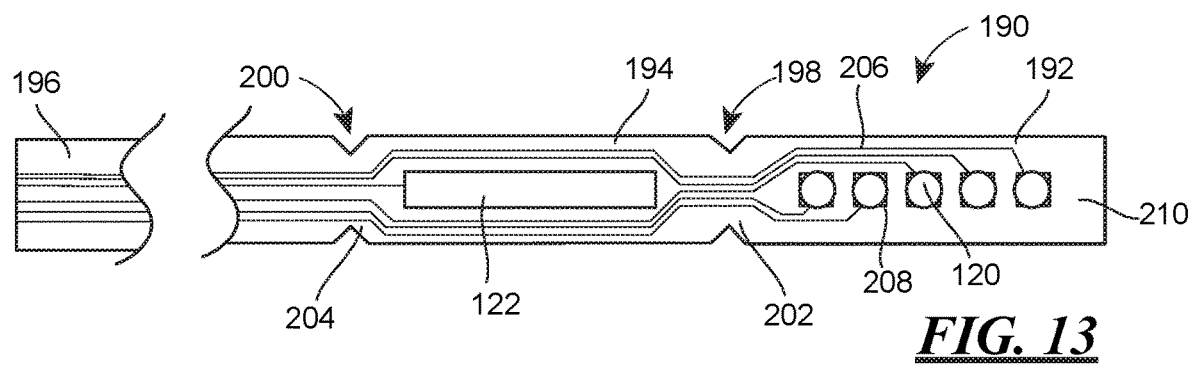
FIG. 13 is an enlarged, plan view of a flexible substrate with at least one light emitter and at least one light sensor formed thereon.

As illustrated in FIG. 13, the substrate 190 includes three sections 192, 194, 196 that are connected by two living hinges 198, 200. The living hinges 198, 200 permit the sections 192, 194, 196 to be deformed or bent relative to each other for assembly with the remainder of the instrument 106, and for at least sections 194, 196 to move relative to each other in accordance with the motion of one or both of the jaws 180, 182. The hinges 198, 200 are defined by bridges 202, 204 of the substrate 190 that connect ends of the three sections 192, 194, 196. According to the illustrated embodiment, the emitter 120 is attached to first section 192, while the sensor 122 is attached to the second section 194.

As illustrated, a plurality of conductors 206 and pads 208 are formed on at least one surface 210 of the substrate 190. The emitter 120 and sensor 122 are attached to first and second sets of pads 208. The conductors 206 are attached to the pads 208, and ultimately attach the pads 208 to the controller 124.

Figure 14:
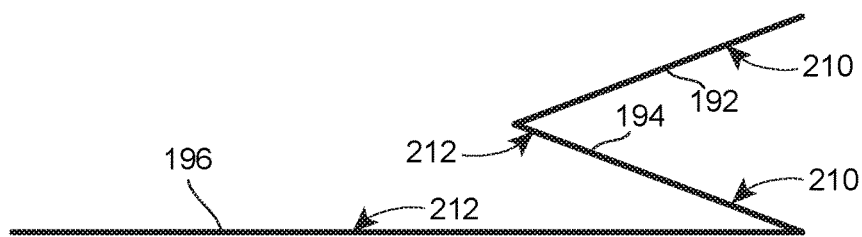
FIG. 14 is an enlarged, side view of the flexible substrate of FIG. 13 folded for assembly with a two-jaw surgical instrument.
Figure 15:
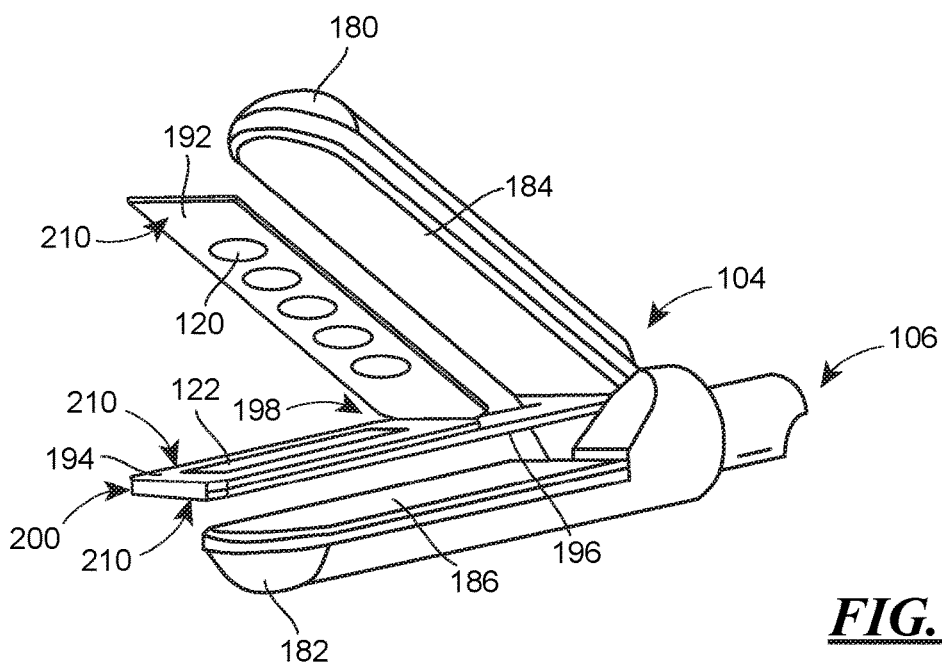
FIG. 15 is an enlarged, side view illustrating how the flexible substrate of FIG. 13 may be assembled with a two-jaw surgical instrument.

As illustrated in FIG. 14, the substrate 190 is bent so that the first and second sections 192, 194 may be attached to the jaws 180, 182, while the third section 196 may be disposed into the shaft. In particular, the first and second sections 192, 194 may be bent about living hinge 198 so that the first surfaces 210 of the first and second sections 192, 194 face each other. On the other hand, the second and third sections 194, 196 are bent about living hinge 200 so that a second surface 212 of the second and third sections 194, 196 face each other.

According to this embodiment, the third section 196 would be inserted into the inner space of the shaft with the first surface 210 of the substrate 190 facing the inner surface of the shaft. The folded structure of the second and third sections 194, 196 would then be attached to the jaw 182 (e.g., surface 186), while the first section 192 would be attached to jaw 180 (e.g., surface 184). In this fashion, the first section 192 would move with the jaw 180 relative to the second section 194 and jaw 182.

According to a further embodiment similar to that of FIGS. 13-15, the substrate also includes three sections that are connected by two living hinges. The living hinges permit the three sections to be bent relative to each other for assembly with the remainder of the instrument 106, and for at least two sections to move relative to each other in accordance with the motion of one or both of the jaws 180, 182. The hinges are defined by bridges of the substrate that connect ends of the three sections. The emitter 120 is attached to first section, while the sensor 122 is attached to the second section.

The substrate is folded in a fashion similar to that of the embodiment of FIGS. 13-15: the first and second sections may be bent about the first living hinge so that first surfaces of the first and second sections face each other, while the second and third sections are bent about the second living hinge so that second surfaces of the second and third sections face each other. Unlike the embodiment of FIGS. 13-15, the second and third sections are attached to opposite surfaces of the jaw 182, while the first section is attached to the opposed jaw 180. As such, the first section can move relative to the second section, while the second section is not folded with such a sharp bend at the hinge as is in the embodiment of FIGS. 13-15. This may reduce the stresses caused by bending the substrate to have the second surfaces of the second and third sections facing each other.

Having discussed the structure, operation and assembly of various embodiments utilizing a flexible substrate, a further embodiment of a two-jaw surgical instrument having at least one light emitter and at least one light sensor is illustrated in FIGS. 16-19. While the embodiment utilizes conductors in the form of leads or wires to connect the at least one light emitter and at least one light sensor to the remainder of the equipment, the shape and arrangement of the jaws according to the embodiment of FIGS. 16-18 may be utilized to permit the passage of flexible substrates into and out of the shaft of the surgical instrument as well.

Figure 16:
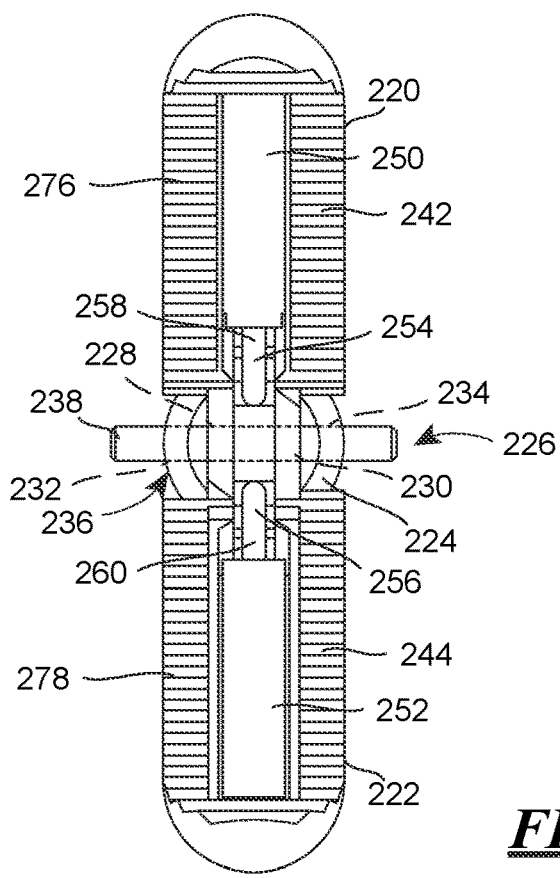
FIG. 16 is an enlarged frontal view of an embodiment of a two jaw surgical instrument with at least one light emitter and at least one light sensor attached thereto.

FIGS. 16-19 illustrate a two-jaw surgical instrument including a first jaw 220 and a second jaw 222. The first and second jaws 220, 222 are attached to a shaft 224 at a pivot or hinge 226. As best seen in FIG. 16, each of the jaws 220, 222 has an opening or passage 228, 230 that is aligned with openings or passages 232, 234 in a distal end 236 of the shaft 224. A pin or rod-shaped fastener 238 is disposed through the openings or passages 228, 230, 232, 234 to join the jaws 220, 222 to the shaft 224. While the ends of the fastener 238 are illustrated as extending past an outer surface of the shaft 224 in FIGS. 16 and 17, the ends may terminate close to the outer surface according to other embodiments.

Figure 18:
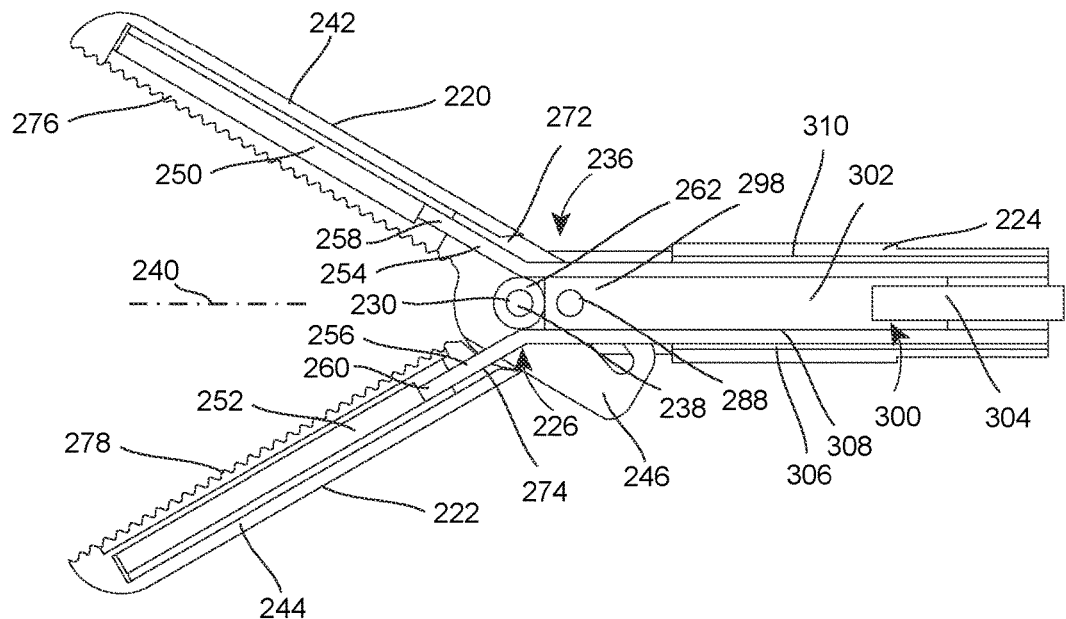
FIG. 18 is a partial cross-sectional view of the two jaw surgical instrument of FIG. 16, with a portion of the jaws removed to expose leads coupled to the at least one light emitter and the at least one light sensor interior to the jaws.
Figure 19:
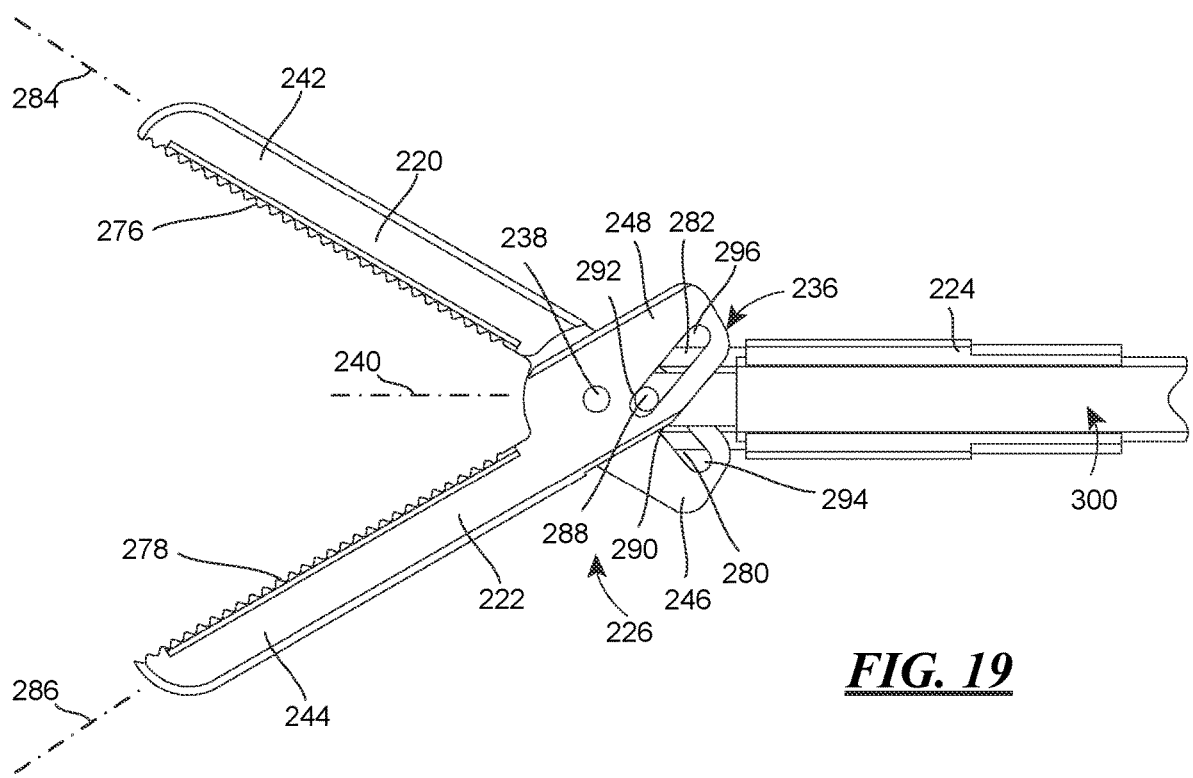
FIG. 19 is a partial cross-sectional view of the two jaw surgical instrument of FIG. 16, with a portion of the shaft wall removed to illustrate an embodiment of a mechanism for moving the jaws.

As illustrated in FIGS. 18 and 19, the shaft 224 has a longitudinal axis 240 that extends generally from the distal end 236 to a proximal end, where the handle or grip may be disposed. As best seen in FIG. 19, each jaw 220, 222 has a first, distal arm or end 242, 244 that depends from the hinge 226 in a distal direction along the longitudinal axis 240 and a second, proximal arm or end 246, 248 that depends from the hinge in a proximal direction along the longitudinal axis 240. As seen in FIGS. 16 and 18, at least one light emitter 250 is attached to the distal end 242 of the jaw 220, while at least one light sensor 252 is attached to the distal end 244 of the jaw 222.

As illustrated in FIGS. 16 and 18, the surgical instrument may include one or more leads 254, 256 to couple the at least one light emitter 250 and the at least one light sensor 252 to the remainder of the equipment, which may be located at the proximal end of the shaft 224 or may be even further removed from the distal end 236 of the shaft 224. While the lead 254 and the lead 256 may actually include a plurality of leads or wires (e.g., six wires for the at least one light emitter 250 and six wires for the at least one light sensor 252, which wires may be, for example, an insulated stranded wire or insulated solid core wire having a gauge of AWG 32 or 36, preferably in ribbon cable form) that may or may not be assembled as a single unit, for ease of discussion, the leads 254, 256 will be each be referred to in the singular. The lead 254 is coupled at a distal end 258 to the at least one light emitter 250, and the lead 256 is coupled at a distal end 260 of the at least one light sensor 252, while the proximal ends of both leads 254, 256 may be coupled to the remainder of the equipment.

Figure 17:
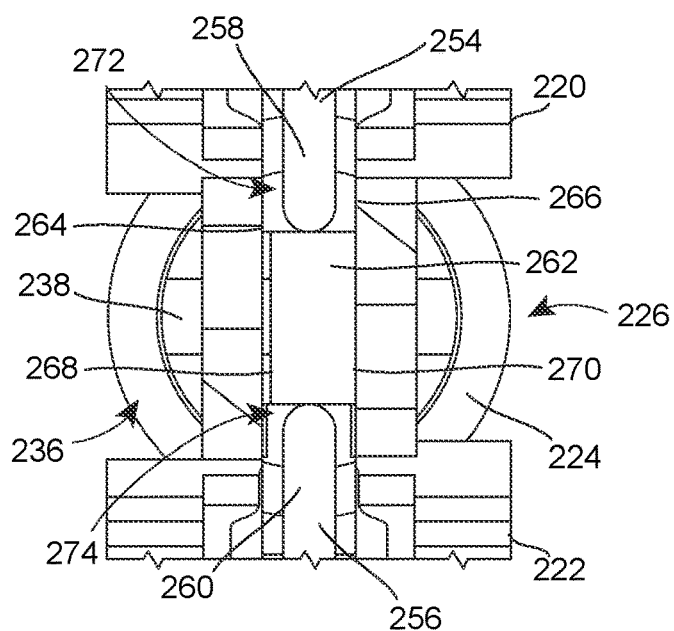
FIG. 17 is an enlarged, partial frontal view of the two-jaw surgical instrument of FIG. 16.

To accommodate the leads 254, 256, the distal arms or ends 242, 244 are spaced from each other to permit the leads to exit/enter the shaft 224 that is hollow. As best seen in FIG. 17, a spacer 262 is introduced between inwardly facing or inner surfaces 264, 266 of the jaws 220, 222. The spacer 262 may have a first end 268 that abuts the surface 264, and a second end 270 that abuts the surface 266. As illustrated, the spacer 262 is formed integrally (i.e., as one piece) with the jaw 222, although this need not be the case according to other embodiments.

The spacer 262 defines clearances 272, 274 for the leads 254, 256, as seen in FIGS. 16 and 17. The clearances 272, 274 are volumes through which the leads 254, 256 may exit/enter the shaft 224 without the other structures of the jaws 220, 222 impinging on the leads 254, 256 so as to crimp, pinch or crush the leads 254, 256. The clearances 272, 274 may be defined by the inner surfaces 264, 266 of the jaws 220, 222 and the spacer 262. The clearances 272, 274 may have a cross-sectional area of 1.75 mm wide and 1.25 mm tall, for example.

The surgical instrument also includes a mechanism for opening and closing the jaws 220, 222 (i.e., moving surfaces 276, 278 further apart and closer together). While an embodiment of such a mechanism is illustrated in FIGS. 18 and 19, other mechanisms may be used to open and close the jaws 220, 222. For example, while the illustrated mechanism is positioned closer to the proximal end of the shaft 224 than the distal end 236 (relative to the hinge 226) in FIGS. 18 and 19, other mechanisms operate the jaws 220, 222 from the other side of the hinge 226.

As illustrated, the proximal ends 246, 248 of the jaws 220, 222 each have a race or slot 280, 282 that is formed through the ends 246, 248. The slots 280, 282 are arranged generally along a longitudinal axis 284, 286 of the respective jaw 220, 222. As illustrated, the slots 280, 282 may be disposed at a slight angle to the respective longitudinal axis 284, 286. A pin, rod or cam 288 is received within the slots 280, 282, and may move along the slots 280, 282 between a first end 290, 292 of the slots 280, 282 and a second end 294, 296 of the slots 280, 282.

The pin 288 is attached to a distal end 298 of an actuator 300, which may include a yoke 302 and a push rod 304 as illustrated. The proximal end of the actuator 300 may be attached to a mechanism such as a scissors grip or a trigger grip, which may be disposed at the proximal end of the shaft 224. The movement of the actuator 300 in a generally longitudinal direction to the right, with reference to the orientation illustrated in FIG. 19, will cause the pin 288 to move from the first ends 290, 292 to the second ends 294, 296 of the slots 280, 282, which will cause the surfaces 276, 278 to move toward each other (i.e., to close the jaws 220, 222). The movement of the actuator 300 in a generally longitudinal direction to the left, with reference to the orientation illustrated in FIG. 19, will cause the pin 288 to move from the second ends 294, 296 to the first ends 290, 292 of the slots 280, 282, which will cause the surfaces 276, 278 to move apart (i.e., to open the jaws 220, 222, as illustrated in FIG. 19). The actuator 300 may be biased (e.g., through the use of a spring or other resilient member) toward the left so that the jaws 220, 222 are open by default.

Where, as illustrated in FIG. 18, the actuator 300 is centrally disposed within the shaft 224, an inner surface 306 of the shaft 224 and an outer surface 308 of the actuator 300 define a passage 310 between the distal end 236 and the proximal end of the shaft 224. The passage 310 may be annular, or may be some other shape. The passage 310 may be discontinuous in certain embodiments, such that there is a discrete section aligned with clearance 272 and a discrete section aligned with clearance 274. The passage 310 permits the leads 254, 256 to extend or depend between the distal end 236 and proximal end of the shaft 224.

Additional details regarding the sensor, the controller and other ancillary equipment are now provided.

The light emitter 120 may include one or more elements, as referenced above. According to an embodiment schematically illustrated in FIG. 6, the light sensor 122 may include a first light emitter 120-1, a second light emitter 120-2, and a third light emitter 120-3. All of the light emitters may be adapted to emit light at a particular wavelength (e.g., 660 nm), or certain emitters may emit light at different wavelengths than other emitters. Each light emitter may be a light emitting diode, for example.

As to those embodiments wherein the light emitter 120 is in the form of an array including one or more light emitting diodes, as is illustrated in FIG. 6 or any one of FIGS. 11-15, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 122 also may include one or more elements. Again, according to the embodiment illustrated in FIG. 6, the light sensor 122 may include a first light sensor 122-1, a second light sensor 122-2, an n-th light sensor 122-n, and so on. As was the case with the light emitters 120-1, 120-2, 120-3, the light sensors 122-1, 122-2, 122-3 may be arranged in an array, and the discussion about the arrays above applied with equal force here.

In fact, where the array of light sensors 122 includes a row of light sensors (such as in FIG. 6), the array 122 may be referred to in the alternative as a linear array. The individual light sensors of the array 122 may be disposed adjacent each other, or the light sensors may be spaced from each other. It may even be possible for the individual light sensors that define a row of light sensors to be separated from each other by light sensors that define a different row or column of the array. According to a particular embodiment, however, the array may comprise a charge coupled device (CCD), and in particular linear CCD imaging device comprising a plurality of pixels. As a further alternative, a CMOS sensor array may be used.

While the arrangement of the light emitter 120 and the light sensor 122 may vary relative to the reflectance-based embodiments of FIGS. 3-5, it is equally true that the light emitter 120 and the light sensor 122 may involve a plurality of elements.

Contrasting the arrangement illustrated in FIGS. 3-5 with that of FIG. 6 then, the light emitter 120 and light sensor 122 are disposed generally facing in a common direction (i.e., the direction of the tissue sample of interest). This does not require the emitter 120 and the sensor 122 to be generally disposed in a common plane, although this is preferred. According to certain embodiments, the emitter 120 and sensor 122 may be formed integrally (i.e., as one piece) with a surgical instrument 106 (see FIGS. 3-5), although other options are possible, as discussed below. In this manner, light emitted by the emitter 120 and scattered by the tissue of interest may be captured by the light sensor 122.

Further, it is believed that the spacing between the emitter 120 and the sensor 122 may influence the light received by the sensor 122. As presently understood, after photons leave the emitter 120 in contact with tissue, an ensemble of independent photons return to the surface and reach the sensor 122. Some of the detected photons travel a short distance from the plane of the emitter and detector and exit at the site of the sensor 122, while some photons travel farther into the tissue before exiting at the surface without being absorbed (photons that are absorbed cannot contribute to the photocurrent). Path length distributions and the penetration depth of photons that reach the sensor 122 vary as a function of emitter-sensor separation, with maximum effective photon depth penetration values several times greater than the physical emitter-sensor separation. For example, it has been determined that a spacing between the emitter 120 and the sensor 122 of 5 mm may permit detection of vessels from 0 mm to 12 mm from the surface of the tissue.

Changes in blood volume, due to differences in systolic and diastolic pressures within a tissue-embedded artery, affect the relative number of long-traveling photons that survive and reach the sensor 122. The temporally observed difference in the number of long-traveling photons that results from the presence of an artery in the photon trajectory is responsible for the pulsatile (AC) signal. For a small source-detector separation, detected photons traversing the shorter distances are less exposed to the cycling blood of an artery at a greater depth below the tissue surface, and therefore survive with a more uniform likelihood between systolic and diastolic conditions. With an increased source-detector separation, a higher percentage of photons that reach the sensor 122 will be long-traveling photons, resulting in larger detected pulse amplitudes. Therefore, it is believed that increasing the spacing between the emitter 120 and the sensor 122 may permit the light to penetrate even deeper into the tissue, permitting vessel detection at even greater depths.

It is further believed that adjusting the angle of the emitter 120 and/or sensor 122 may provide a similar effect. That is, similar to the way in which a change in the linear distance between the emitter 120 and the sensor 122 allows for the sampling of a different proportion of long-traveling photons at the surface sensor 122, a variation in angle of the emitter 120 and/or sensor 122 can change the depth and the distance to which the photons travel before being sampled by the sensor 122. Consequently, changes in the angle of the emitter and/or sensor are believed to permit the depth at which vessels can be detected by the instrument 106 to be varied.

Thus, according to the embodiments described herein, the emitter 120 and sensor 122 may be disposed to be mounted in a fixed relationship to each other, or a moveable or adjustable relationship. In particular, FIGS. 3 and 4 illustrate embodiments wherein emitter 120 and sensor 122 are at a fixed spacing relative to each other, and also have a fixed angular relationship between the emitter 120 and the sensor 122. Such an embodiment would permit the user to be confident that the vessels detected are within, for example, 12 mm from the working end 104 of the instrument 106. By contrast, the embodiment of FIG. 5 has the sensor 122 mounted in a first jaw 180 of the instrument 106 and the emitter 120 mounted in a second jaw 182 of the instrument 106. Such an embodiment would permit the user to vary the depth of detection simply by varying the distance between the jaws 180, 182 of the instrument 106: with the jaws 180, 182 closed, the user may probe for shallow vessels (i.e., vessels disposed within 12 mm of the tissue surface), while with the jaws 180, 182 open, the user may probe for deeper vessels (i.e., vessels disposed greater than 12 mm below the tissue surface). According to the embodiment illustrated in FIG. 5, the control structure for operating the jaws 180, 182 may include a mechanism for modifying the distance between the jaws 180, 182 in a controlled fashion (e.g., in discrete increments) so that the user can determine the jaw spacing (and thus the detection depth) without visualization of the jaws 180, 182.

As mentioned above, the light emitter 120 of any of FIGS. 3-5 may include one or more elements. According to such an embodiment, all of the elements may be adapted to emit light at a particular wavelength (e.g., 660 nm), or certain elements may emit light at different wavelengths than other elements. It is believed that a system with multiple light emitters 120 and/or multiple sensors 122 will increase the signal-to-noise ratio and the spatial resolution compared to a system containing a single emitter 120 and sensor 122.

As to those embodiments wherein the light emitter 120 is in the form of an array including one or more light emitting diodes, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 122 according to the embodiments of FIGS. 3-5 also may include one or more individual elements. As was the case with the light emitter 120, the elements of the light sensor 122 may be arranged in an array, and the discussion about the arrays above applied with equal force here.

In addition, the light sensor 122 may include a mechanism for physically excluding photons reaching the sensor 122 from a range of angles. This mechanism can consist of a mask or grated layer to physically filter any photons that are not reaching the sensor 122 at a nearly perpendicular angle. It has been observed that the mean depth penetration of the photons leaving the emitter 120 is equal to just over half the distance of source-detector separation (~2.5 mm penetration for our 5 mm spacing). This mechanism will increase the proportion of long-traveling and deep penetrating photons that are received by the sensor 122 thus increasing the depth at which the vessels can be detected by the instrument.

As to all of the foregoing embodiments, the system 100 may include hardware and software in addition to the emitter 120, sensor 122, and controller 124. For example, where more than one emitter 120 is used, a drive controller may be provided to control the switching of the individual emitter elements. In a similar fashion, a multiplexer may be provided where more than one sensor 122 is included, which multiplexer may be coupled to the sensors 122 and to an amplifier. Further, the controller 124 may include filters and analog-to-digital conversion as may be required.

According to certain embodiments, the splitter 126 and the analyzer 128 may be defined by one or more electrical circuit components. According to other embodiments, one or more processors (or simply, the processor) may be programmed to perform the actions of the splitter 126 and the analyzer 128. According to still further embodiments, the splitter 126 and the analyzer 128 may be defined in part by electrical circuit components and in part by a processor programmed to perform the actions of the splitter 126 and the analyzer 128.

For example, the splitter 126 may include or be defined by the processor programmed to separate the first pulsatile component from the second non-pulsatile component. Further, the analyzer 128 may include or be defined by the processor programmed to determine the presence of (or to quantify the size of, for example) the vessel V within the region 102 proximate to the working end 104 of the surgical instrument 106 based on the first pulsatile component. The instructions by which the processor is programmed may be stored on a memory associated with the processor, which memory may include one or more tangible non-transitory computer readable memories, having computer executable instructions stored thereon, which when executed by the processor, may cause the one or more processors to carry out one or more actions.

Figure 20:
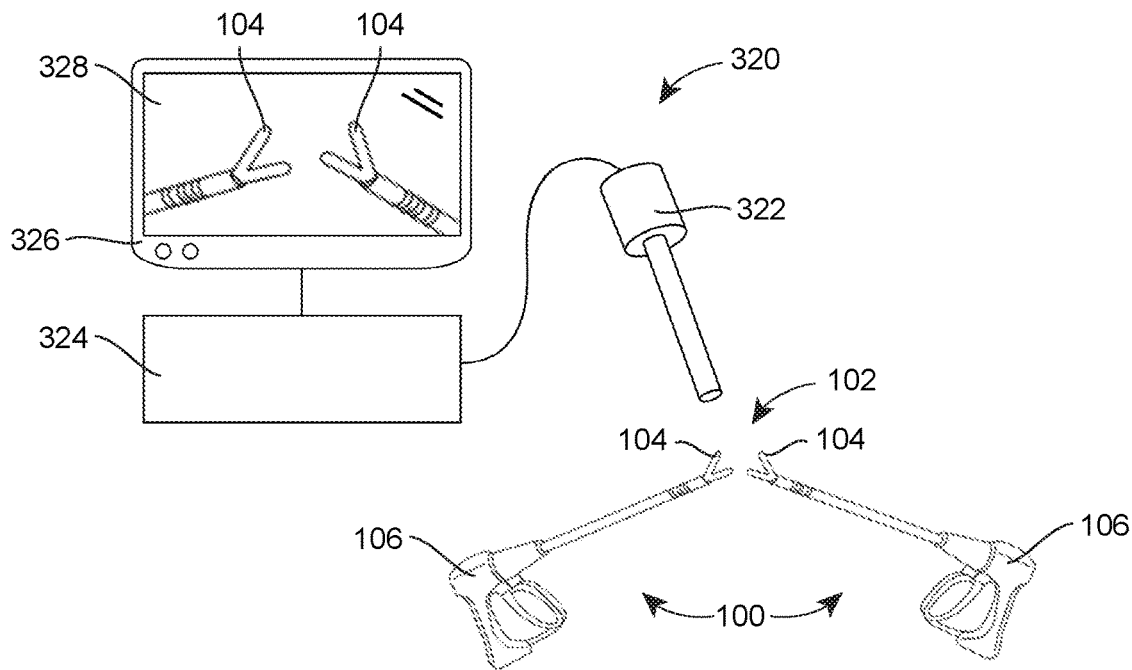
FIG. 20 is a schematic diagram of a surgical system according to an embodiment of the present disclosure, in combination with an embodiment of a video system, illustrating the surgical system in use with the video system.
Figure 21:
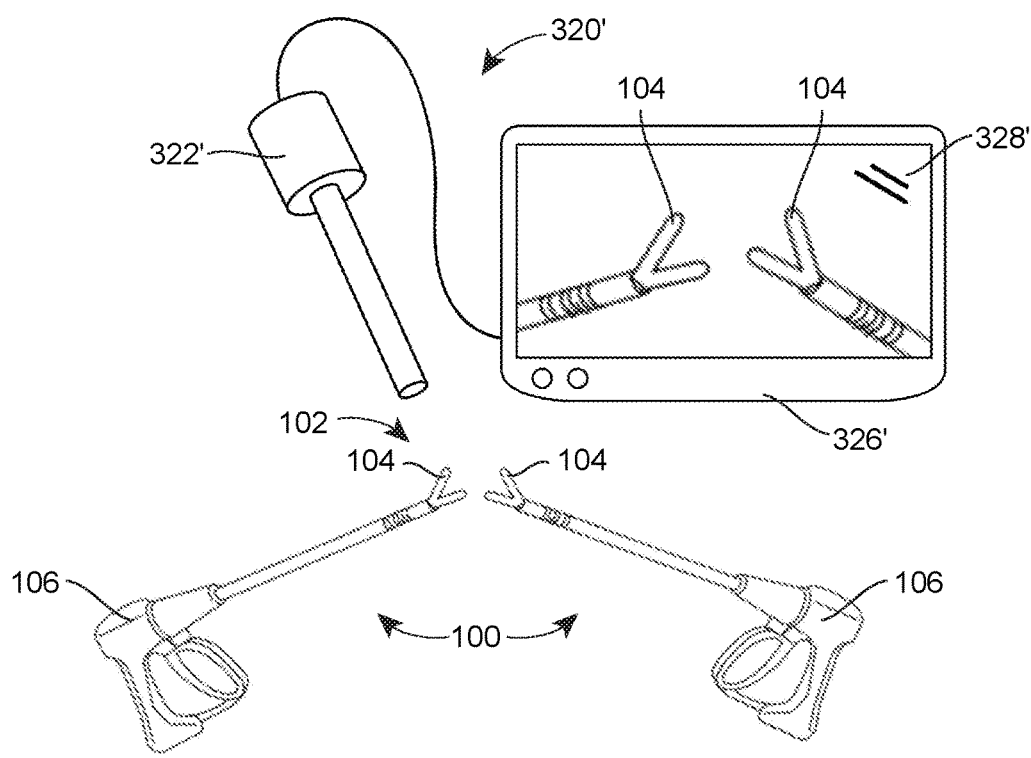
FIG. 21 is a schematic diagram of a surgical system according to an embodiment of the present disclosure, in combination with another embodiment of a video system, illustrating the surgical system in use with the video system.

FIGS. 19 and 20 illustrate embodiments of the surgical system 100 in combination with embodiments of a video system 320, such as may be used conventionally during minimally invasive surgery or laparoscopic surgery, for example.

In the embodiment of FIG. 19, the video system 320 includes a video camera or other image capture device 322, a video or other associated processor 324, and a display 326 having a viewing screen 328. As illustrated, the video camera 322 is directed at the region 102 proximate the working ends 104 of two surgical instruments 106. As illustrated, both of the surgical instruments 106 are part of an embodiment of a surgical system 100. The other elements of the surgical system 100 are omitted for ease of illustration, although it will be noted that elements of the system 100, such as the splitter 126 and the analyzer 128, may be housed in the same physical housing as the video processor 324. The signal from the video camera 322 is passed to the display 326 via the video processor 324, so that the surgeon or other member of the surgical team may view the region 102 as well as the working ends 104 of the surgical instruments 106, which are typically inside the patient.

FIG. 20 illustrates another embodiment of a video system 320 that can be used in conjunction with an embodiment of the surgical system 100. According to this embodiment, the video processor 324 is not disposed in a housing separate from the video camera 322', but is disposed in the same housing as the video camera 322'. According to a further embodiment, the video processor 324 may be disposed instead in the same housing as the remainder of the display 326' as the display screen 328'. Otherwise, the discussion above relative to the embodiment of the video system 320 illustrated in FIG. 19 applies equally to the embodiment of the video system 320 illustrated in FIG. 20.

Figure 2:
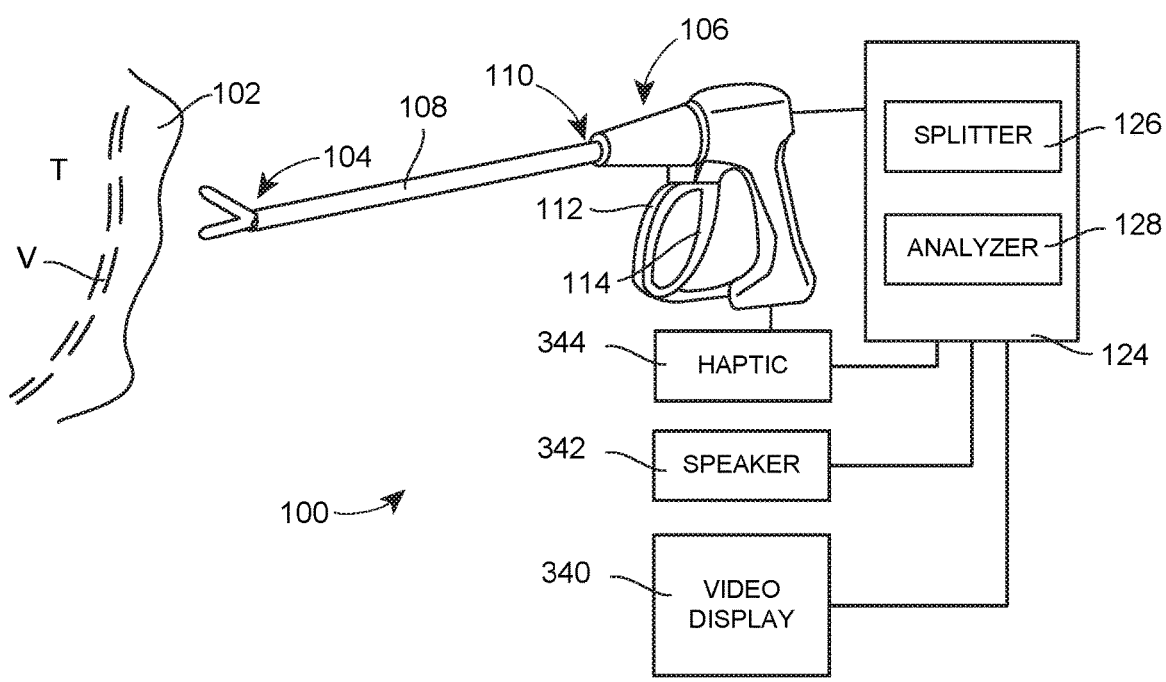
FIG. 2 is a schematic diagram of a surgical system according to another embodiment of the present disclosure.

The system 100 may include output devices such as illustrated in FIGS. 1 and 2, which may incorporate elements of the system 320. For example, an alert may be displayed on a video monitor 340 being used for the surgery (e.g., the display 326, 326' in FIGS. 19 and 20), or may cause an image on the monitor to change color or to flash, change size or otherwise change appearance. The auxiliary output may also be in the form of or include a speaker 342 that provides an auditory alarm. The auxiliary output also may be in the form of or may incorporate a safety lockout associated with the surgical instrument 106 that interrupts use of the instrument 106. For example, the lockout could prevent ligation or cauterization where the surgical instrument 106 is a thermal ligature device. As a still further example, the auxiliary output also may be in the form of a haptic feedback system, such as a vibrator 344, which may be attached to or formed integral with a handle or handpiece of the surgical instrument 106 to provide a tactile indication or alarm. Various combinations of these particular forms of the auxiliary output may also be used.

As noted above, the surgical instrument 106 may be a thermal ligature device in one embodiment. In another embodiment, the surgical instrument 106 may simply be a grasper or grasping forceps having opposing jaws. According to still further embodiments, the surgical instrument may be other surgical instruments such as irrigators, surgical staplers, clip appliers, and robotic surgical systems, for example. According to still other embodiments, the surgical instrument may have no other function that to carry the user interface and sensor and to place them within a surgical field. The illustration of a single embodiment is not intended to preclude the use of the system 100 with other surgical instruments or tools 106.

In conclusion, although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

What is claimed is:

1. A surgical system comprising:
a tubular shaft having a proximal end and a distal end;
a first jaw and a second jaw pivotally attached at the distal end of the tubular shaft; and
at least one light emitter and at least one light sensor, the at least one light emitter being disposed along a surface of the first jaw and the at least one light sensor being disposed along a surface of the second jaw with the surface of the first jaw facing the surface of the second jaw, each of the at least one light emitter and at least one light sensor coupled to at least one lead,
the first and second jaws each having an inwardly facing surface, the inwardly facing surface of the first jaw disposed transverse to the surface of the first jaw along which the at least one light emitter is disposed and the inwardly facing surface of the second jaw disposed transverse to the surface of the second jaw along which the at least one light sensor is disposed, and the inwardly facing surfaces define at least in part one or more clearances therebetween in which the at least one lead coupled to the at least one light emitter and the at least one lead coupled to the at least one light sensor are disposed,
wherein a spacer is disposed in a space between the inwardly facing surfaces of the first and second jaws, the inwardly facing surfaces and the spacer defining the one or more clearances in which the at least one lead coupled to the at least one light emitter and the at least one lead coupled to the at least one light sensor are disposed.

2. The surgical system according to claim 1, wherein the one or more clearances comprise first and second clearances, a first lead of the at least one leads disposed through the first clearance and a second lead of the at least one leads disposed through the second clearance, the first lead coupled to the at least one light emitter and the second lead coupled to the at least one light sensor.

3. The surgical system according to claim 1, wherein the distal end of the shaft has openings, each of the first and second jaws has an opening aligned with the openings in the distal end of the shaft, and a rod-shaped fastener is disposed through the spacer, the openings in the distal end of the shaft, and the openings in the first and second jaws to pivotally attach the first and second jaws to the distal end of the shaft.

4. The surgical system according to claim 1, wherein each of the at least one leads comprises a plurality of wires.

5. The surgical system according to claim 1, further comprising a mechanism for opening and closing the first and second jaws, wherein:
the first and second jaws each having a proximal end with a slot formed through the ends, the slots arranged generally along a longitudinal axis of the first and second jaws,
a pin is disposed within the slots, the pin being movable along the slots between a first end of the slots and a second end of the slots, and
an actuator, the pin attached to a distal end of the actuator.

6. The surgical system according to claim 5, wherein the actuator is centrally disposed within the shaft, the shaft having an inner surface and the actuator having an outer surface, the inner surface and the outer surface defining a passage that permits each of the at least one leads to extend between the distal end and the proximal end of the shaft.

7. The surgical system according to claim 5, wherein the actuator is attached to a scissors grip or a trigger grip disposed at the proximal end of the shaft.

8. The surgical system according to claim 5, wherein the actuator is biased through the use of a resilient member so that the first and second jaws are open by default.

9. The surgical system according to claim 8, wherein the resilient member is a spring.

* * * * *